US009376666B2

(12) United States Patent
Reneker et al.

(10) Patent No.: US 9,376,666 B2
(45) Date of Patent: Jun. 28, 2016

(54) NANOFIBERS WITH HIGH ENZYME LOADING FOR HIGHLY SENSITIVE BIOSENSORS

(75) Inventors: Darrell H. Reneker, Akron, OH (US); Songtao Wu, St. Paul, MN (US); Ping Wang, North Oaks, MN (US); Hongfei Jia, Ann Arbor, MI (US); Ravindrabharathi Narayanan, St. Paul, MN (US)

(73) Assignee: The University of Akron, Akron, OH (US)

( * ) Notice: Subject to any disclaimer, the term of this patent is extended or adjusted under 35 U.S.C. 154(b) by 938 days.

(21) Appl. No.: 12/673,857

(22) PCT Filed: Aug. 18, 2008

(86) PCT No.: PCT/US2008/009835
§ 371 (c)(1),
(2), (4) Date: Jun. 1, 2011

(87) PCT Pub. No.: WO2009/029180
PCT Pub. Date: Mar. 5, 2009

(65) Prior Publication Data
US 2011/0229916 A1 Sep. 22, 2011

Related U.S. Application Data

(60) Provisional application No. 60/965,089, filed on Aug. 17, 2007.

(51) Int. Cl.
| *C12N 11/16* | (2006.01) |
| *C12N 9/04* | (2006.01) |
| *C12N 11/04* | (2006.01) |
| *C12N 11/08* | (2006.01) |
| *C12Q 1/00* | (2006.01) |

(52) U.S. Cl.
CPC .............. *C12N 9/0006* (2013.01); *C12N 11/04* (2013.01); *C12N 11/08* (2013.01); *C12Q 1/006* (2013.01); *C12Y 101/03004* (2013.01)

(58) Field of Classification Search
None
See application file for complete search history.

(56) References Cited

U.S. PATENT DOCUMENTS

| 5,914,367 | A | 6/1999 | Dordick et al. | |
| 6,382,526 | B1 | 5/2002 | Reneker | |
| 6,520,425 | B1 | 2/2003 | Reneker | |
| 6,695,992 | B2 | 2/2004 | Reneker | |
| 6,821,479 | B1 * | 11/2004 | Smith et al. | 422/1 |
| 7,662,332 | B2 * | 2/2010 | Chu et al. | 264/465 |
| 2006/0094096 | A1 | 5/2006 | Wang et al. | |
| 2006/0134716 | A1 | 6/2006 | Gourma | |

FOREIGN PATENT DOCUMENTS

WO  WO 03-106655  * 12/2003

OTHER PUBLICATIONS

Lin, Yuehe, et al., "Glucose Biosensors Based on Carbon Nanotube Nanoelectrode Ensembles", Nano Letters, vol. 4, No. 2, 2004, pp. 191-195.
Newman, J.D., et al., "Enzymatic Biosensors", Molecular Biotechnology, vol. 32, No. 3, 2006, pp. 249-268.
Zhang, Yanzhong, et al., "Recent development of Polymer Nanofibers for Biomedical and Biotechnological Applications". Journal of Materials Science: Materials in Medicine, vol. 16, 2005, pp. 933-946.
Schuhmann, Wolfgang, "Amperometric Enzyme Biosensors Based on Optimised Electron-transfer Pathways and Non-manual Immobilisation Procedures", Reviews in Molecular Biotechnology, vol. 82, 2002, pp. 425-441.
Wu, Lili, et al., "Immobilization of Cellulase in Nanofibrous PVA Membranes by Electrospinning", Journal of Membrane Science, vol. 250, 2005, pp. 167-173.
Jia, Hongfei, et al., "Enzyme-Carrying Polymeric Nanofibers prepared via Electrospinning for Use as Unique Biocatalysts", Biotechnology Prog., vol. 18, 2002, pp. 1027-1032.
Lee, Dohoon, et al., "Simple Fabrication of a Highly Sensitive and Fast Glucose Biosensor Using Enzymes Immobilized in Mesocellular Carbon Foam", Advanced Materials, vol. 17, 2005, pp. 2828-2833.
Lee, Seung-Wuk and Angela M. Belcher, "Virus-Based Fabrication of Micro- and Nanofibers Using Elctrospinning", Nano Letters, vol. 4, No. 3, 2004, pp. 387-390.
Manesh, K.M., et al., "Electrospun Poly(vinylidene fluoride)/ Poly(aminophenylboronic acid) Composite Nanofibrous Membrane as a Novel Glucose Sensor", Analytical Biochemistry vol. 360, 2007, pp. 189-195.
Herricks, Thurston E., et al., "Direct Fabrication of Enzyme-carrying polymer Nanofibers by Electrospinning", Journal of Materials Chemistry, vol. 15, 2005, pp. 3241-3245.
Jayesh Doshi and Darrell H. Reneker, "Electrospinning Process and Applications of Electrospun Fibers", Journal of Electrostatics, vol. 35, 1995, pp. 151-160.
Theron, A., et al., "Electrostatic Field-assisted alignment of Electrospun Nanofibres", Nanotechnology, vol. 12, 2001, pp. 384-390.
Jiangbing, Xie and You-Lo Hsieh, "Ultra-high Surface Fibrous Membranes From Electrospinning of Natural Proteins: Casein and Lipase Enzyme", Journal of Materials Science 28, 2003, pp. 2125-2133.
Sawicka, Katarzyna, et al., "Electrospun Biocomposite Nanofibers for Urea Biosensing", Sensors and Actuators B, vol. 108, 2005, pp. 585-588.
Wu, Shuo, et al., "Conductive Mesocellular Silica-Carbon Nanocomposite Foams for Immobilization, Direct Electrochemistry, and Biosensing of Proteins", Advanced Functional Materials, vol. 17, 2007, pp. 585-592.

(Continued)

*Primary Examiner* — Richard Hutson
(74) *Attorney, Agent, or Firm* — Renner Kenner; Greive Bobak; Taylor Weber

(57) ABSTRACT

The invention provides high enzyme loading nanofibers and processes utilized in their fabrication, the nanofibers suitable for use as a new class of highly sensitive and stable biosensors capable of monitoring glucose at low levels. The biosensors, comprising nanofiber enzyme materials fabricated from organic solvent-based polymer-enzyme systems, can be used effectively in non-invasive transdermal biosensing applications.

19 Claims, 8 Drawing Sheets

(56) References Cited

OTHER PUBLICATIONS

Karyakin, Arkady A., et al., "Optimal Environment for Glucose Oxidase in Perfluorosulfonated Lonomer Membranes: Improvement of First-Generation Biosensors", Analytical Chemistry, vol. 74, No. 7, 2002, pp. 1597-1603.

Vamvakaki, Vicky, et al., "Carbon Nanofiber-Based Glucose Biosensor", Analytical Chemistry, vol. 78, No. 15, 2006, pp. 5538-5542.

Angelo Pedicini and Richard J. Farris, "Mechanical Behavior of Electrospun Polyurethane", Science Direct, Polymer 44, 2003, pp. 6857-6862.

Wang, Ping, et al., "Poly(ethylene glycol)-Modified Ligninase Enhances Pentachlorophenol Biodegradation in Water-Solvent Mixtures", Biotechnology, Bioengineering, vol. 64, 1999, pp. 290-297.

Distel, Kelley A., et al., "Biocatalysis Using an Organic-Soluble Enzyme for the Preparation of poly(lactic acid) in Organic Solvents", Bioresource Technology, vol. 96, 2005, pp. 617-623.

Veronese, Francesco M., "Peptide and Protein PEGylation: A Review of Problems and Solutions", Biomaterials, vol. 22, 2001, pp. 405-417.

Toshiaki Mori and Yoshio Okahata, "A Variety of Lipid-coated Clycoside Hydrolases as Effective Glycosyl Transfer Catalysts in homogeneous Organic Solvents", Tetrahedron Letters, vol. 38, No. 11, 1997, pp. 1971-1974.

L.V. Bindhu and T. Emilia Abraham, "Preparation and Kinetic Studies of Surfactant-Horseradish Peroxidase Ion Pared Complex in Organic Media", Biochemical Engineering Journal, vol. 15, 2003, pp. 47-57.

Vikram M. Paradkar and Jonathan S. Dordick, "Aqueous-like Activity of a-Chymotrypsin Dissolved in Nearly Anhydrous Organic Solvents", Journal of American Chemistry Society, vol. 116, 1994, pp. 5009-5010.

Guangyu Zhu and Ping Wang, "Polymer-Enzyme Conjugates Can Self-Assemble at Oil-Water Interfaces and Effect Interfacial Biotransformations", Journal of American Chemical Society, vol. 126, 2004, pp. 11132-11133.

Narayanan, Ravindrabharathi, et al., "Stabilization of interface-binding Chloroperoxidase for Interfacial Biotransformation", Journal of Biotechnology, vol. 128, 2007, pp. 86-92.

Wu, Jin Chuan, et al., "Extraction of Candida Rugosa Lipase From Aqueous Solutions into Organic Solvents by Forming an Ion-paired Complex With AOT", Journal of Chmical Technology Biotechnology, vol. 81, 2006, pp. 1003-1008.

Mehta, S.K., et al., "Effect of Temperature on Critical micelle Concentration and Thermodynamic Behavior of Dodecyldimethylethylammonium Bromide and Dodecyltrimethylammonium Chloride in Aqueous Media", Colloids and Surfaces, A: Physiochem. Eng., Asepects, vol. 255, 2005, pp. 153-157.

Wang, Joseph, et al., "Highly Selective Membrane-Free, Mediator-Free Glucose Biosensor", Analytical Chemistry, vol. 66, No. 21, 1994, pp. 3600-3603.

* cited by examiner

Conditions: 0.7 mg/ml GOx in aq. phase, Toluene as organic solvent, 2mM DDAB, phase ratio of 1:1.

Conditions: 0.7 mg/ml GOx in aq. phase, pH 5.5, 2mM DDAB, phase ratio of 1:1.

Conditions: 0.7 mg/ml GOx in aq. phase, pH 5.5, Toluene as organic solvent, phase ratio of 1:1.

Conditions: pH 5.1, Toluene as organic solvent, 2mM DDAB, phase ratio of 1:1.

Conditions: 0.7 mg/ml GOx in aq. phase, pH 5.5, 2mM DDAB, Toluene as organic solvent.

Conditions: 0.2% Salt, 1THF:3Toluene and 5% GOx.

Conditions: 0.2% Salt, 3THF:1Toluene and 5% GOx.

Conditions: 0% Salt, 3THF:1Toluene and 5% GOx.

Conditions: 0% Salt, 1THF:3Toluene and 5% GOx.

(a) NEM containing 5% (w/w PU) enzyme  (b) NEM containing 20% (w/w PU) enzyme  (c) NEM containing 30% (w/w PU) enzyme.

NANOFIBERS WITH HIGH ENZYME LOADING FOR HIGHLY SENSITIVE BIOSENSORS

FIELD OF THE INVENTION

The present invention generally relates to high enzyme loading nanofibers, processes utilized in their fabrication, and their uses as biosensors. More specifically the invention relates to high enzyme loading nanofibers generated from organic solvent-based systems, including hydrophobic and solvent-based polymer having a high loading of organic-soluble enzymes.

BACKGROUND OF INVENTION

A biosensor is an analytical device which converts a biological response into an electrical signal. Biosensors are used to detect a wide array of chemicals ranging from toxic agents and environmental pollutants to blood sugars. For example, biosensors have used surface enzyme reactions to detect low concentrations of biological substances and gases. The term 'biosensor' is often used to cover sensor devices used to determine the concentration of substances and other parameters of biological interest even where they do not directly utilize a biological system. While enzymes have been used as the biologically responsive material, other biological systems have been utilized as biosensors as well, such as, whole cell metabolism, ligand binding and the antibody-antigen reaction. A biosensor's composition will directly affect its shelf-life, response time, reproducibility, sensitivity, selectivity, and overall effectiveness.

Traditionally, films like cellulose acetate or nafion have been used as coatings to bind, or carry, enzymes in biosensors. The enzymes contained in the membrane or the coating of a biosensor detect analytes in the form of gases or other biological substances. These gases and biological substances act as substrates that attach to receptors located on the enzymes on the surface of a biosensor. Biosensors with higher surface areas allow larger quantities of enzymes to bind to their surface. Increased enzyme levels maximize a biosensor's ability to attract substrates and detect the presence of targeted substances. Nano-structured materials, including nanofibers, are miniscule-sized agents possessing high surface-area-to-mass ratios, rendering them extremely effective biosensors due to their ability to facilitate maximal enzyme loading on their surface.

Nano-structured materials for enzyme immobilization utilize the performance and flexibility of nanofibers in processing and use. These materials are particularly appealing whenever high enzyme loading or large amounts of surface area are of consideration. One method suitable for the preparation of nanofibers is electrospinning. Other methods include, for example, melt blowing of fibers or spinning split bicomponent fibers, among others.

Conventional enzymatic biosensors, however, suffer from a number of drawbacks affecting the mass transfer capabilities of the nano-structured system. Of these, four major drawbacks include low sensitivity, low stability, unreliability at low concentrations of analyte, and enzyme loss due to leaching-out in aqueous environments. In the latter instance, because native enzymes are generally considered water-soluble, extremely high loading is necessary to achieve a structure that retains suitable detection capabilities after the leaching-out of the enzyme.

There is, therefore, a need in the art for a novel method of electrospinning polymer-enzyme solution to prepare nanofibers with high enzyme loading, without serious mass transfer limitations. To address this need, the current invention provides a method of electrospinning polymer-enzyme solution, in an organic, non-aqueous solvent, which can be used to achieve high enzyme loading on polymeric nanofibers. Specifically, the system provided employs hydrophobic, solvent-based polymer electrospinning solution loaded with high amounts, up to 30% w/w of the polymer, organic-soluble enzymes. The use of this system avoids leaching problems experienced by water-soluble enzyme-containing systems, thus rendering the use of the electrospun fibers as biosensors much more feasible. In one embodiment, glucose oxidase is loaded on polyurethane nanofibers for use as a biosensor material.

SUMMARY OF INVENTION

The present invention generally relates to high enzyme loading nanofibers and processes utilized in their fabrication. These nanofibers can be used effectively in the creation of a new class of highly sensitive and stable biosensors. Specifically, a highly sensitive biosensor capable of monitoring glucose at low levels can be used effectively in non-invasive transdermal biosensing applications. Materials with a high content of bioactive agents are in high demand for use in many applications, including functional materials, catalysts, sensors, and drug delivery. The method of the invention provides for fabricating enzyme-carrying nanofibers from organic solvent-based systems, creating material with ideal properties such as high surface area, reusability, thermal stability and mechanical flexibility for use in a new class of sensitive biosensors.

In one embodiment, the present invention relates to electrospun polymer-enzyme composite nanofibers, and to processes for making the same, and to the use thereof as biosensors. The biosensors fabricated find application for use in a variety of areas including, but not limited to, biocatalysis, bioremediation, pollutant degradation, bioactive coatings, drug delivery and tissue engineering. A method by which organic-soluble glucose oxidase, electrospun with organic solutions of polyurethane, is used to form high loading polymer-enzyme composite nanofibers useful for the development of highly sensitive and stable biosensors is also provided.

In another embodiment the present invention relates to a method for producing a biosensor comprising encapsulating an organic-solubilized enzyme by electrospinning a solution comprising a polymer and an organic-soluble enzyme.

In yet another embodiment the present invention relates to a biosensor comprising an organic solubilized enzyme, a polymer and an organic solvent.

In still another embodiment, the present invention relates to a method for producing fibers and/or nanofibers wherein the fibers and/or nanofibers are prepared by electrospinning a polymer-enzyme solution in an organic solvent-based system.

BRIEF DESCRIPTION OF THE DRAWINGS

The following Figures have been added to exemplify the invention set forth herein, and are not intended to limitative thereof.

DETAILED DESCRIPTION OF THE INVENTION

Figure 1:
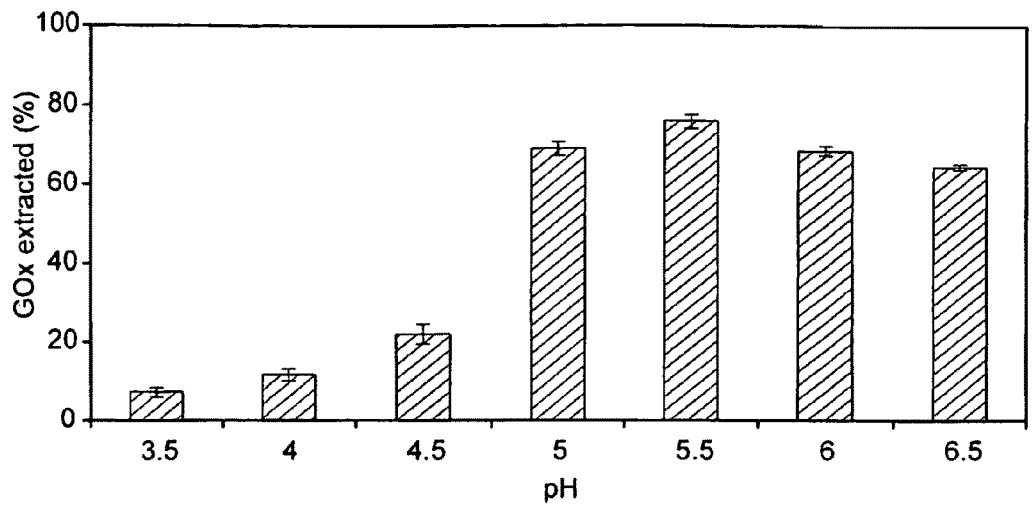
FIG. 1a is a graph of pH vs. percentage of GOx extracted into organic phase; and demonstrates the effect of pH on GOx extraction efficiency
FIG. 1b is a graph of various solvents vs. percentage of GOx extracted into organic phase and demonstrates the effect of various solvents on GOx extraction efficiency.
FIG. 1c is a graph of DDAB concentration vs. percentage of GOx extracted into organic phase and demonstrates the effect of DDAB concentration on GOx extraction efficiency.
FIG. 1d is a graph of GOx concentration vs. percentage of GOx extracted into organic phase and demonstrates the effect of GOx concentration on GOx extraction efficiency.
FIG. 1e is a graph of phase ratio vs. percentage of GOx extracted into organic phase and demonstrates the effect of phase ratio on GOx extraction efficiency.
Figure 1:
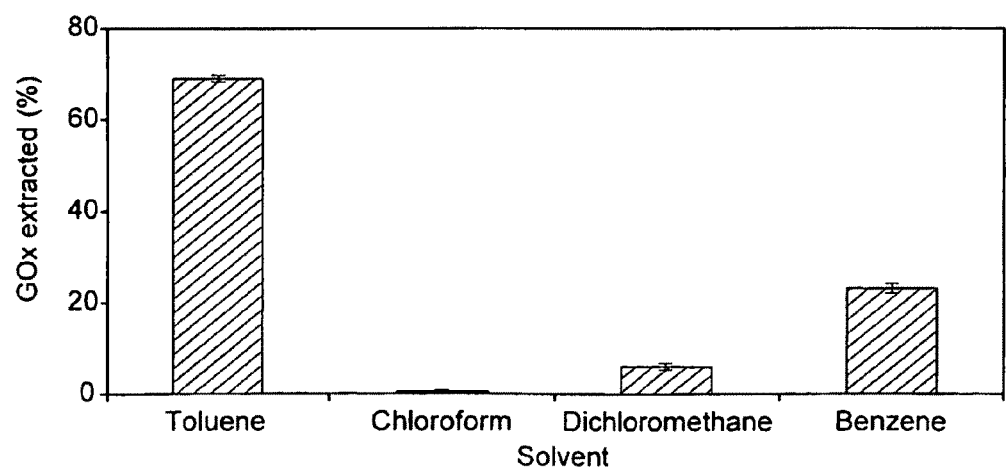
Figure 1:
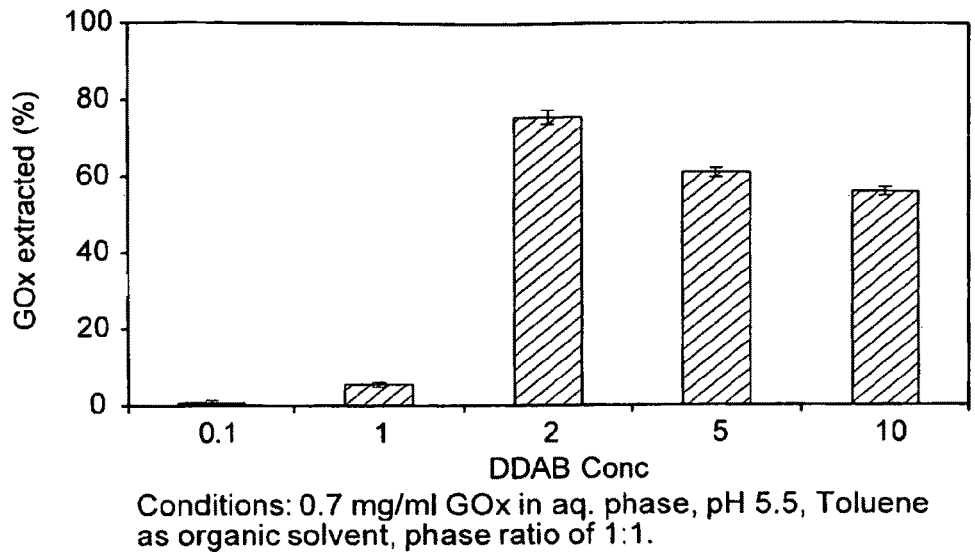
Figure 1:
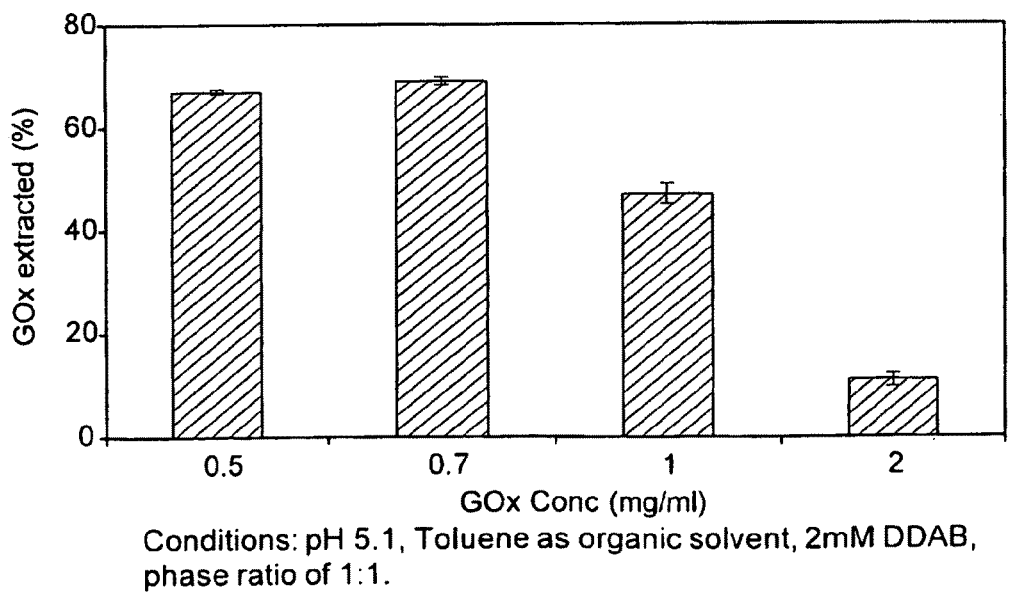
Figure 1:
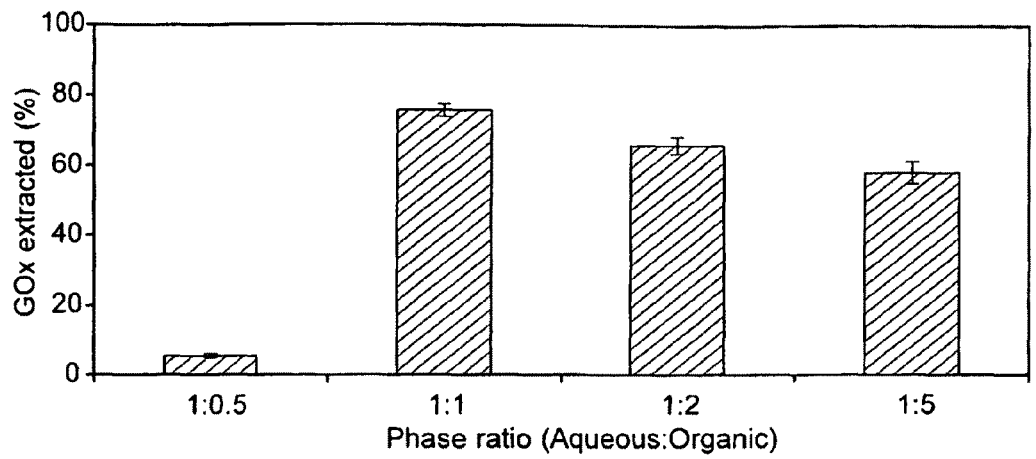

The present invention generally relates to high enzyme loading nanofibers and processes utilized in their fabrication. These nanofibers can be used effectively in the creation of a new class of highly sensitive and stable biosensors. Specifically provided herein is a highly sensitive biosensor capable of monitoring glucose at low levels that can be used effectively in non-invasive transdermal biosensing applications. While a glucose monitoring system is detailed herein as an example of the highly sensitive, stable biosensors made possible by the invention, this system is merely exemplary, and the skilled technician would be capable to applying the principles presented for application to other similar biological systems, such as assays for alcohols, organic acids, urea and other biological metabolites and organic matters that can undergo transformation reaction catalyzed by one or more enzymes such as oxidoreductases, hydrolases and proteases.

Materials with a high content of bioactive agents are in high demand for use in many applications, including functional materials, catalysts, sensors, and drug delivery. This method of fabricating enzyme-carrying nanofibers, or nanofiber enzyme materials, referred to herein as "NEMS", creates material with ideal properties such as high surface area, reusability, thermal stability and mechanical flexibility for use in a new class of highly sensitive biosensors.

In one embodiment, therefore, the present invention provides electrospun polymer-enzyme composite nanofibers, and processes for making the same. One example of the inventive nanofibers and processing provides a method by which organic-soluble glucose oxidase, electrospun with organic solutions of polyurethane, is used to form high enzyme-loading polymer composite nanofibers useful for the development of highly sensitive and stable biosensors.

WO 03/106655, to our common assignee, and incorporated herein by reference in its entirety, provides proteins immobilized on the surface of electrospun nanofibers. While surface attachment of enzymes to nanofibers may lead to high enzyme loading once monolayer attachment is achieved, in some instances only partially covered fibers may result. This is due to the fact that the distribution of functional groups on the surface of the electrospun fibers limits the compatibility between the enzyme and nanofibers. This limited compatibility tends to reduce the uniform distribution of the enzyme. Moreover, this method of immobilization utilizes only the external surface of the nanofibers, leaving the vast internal volume of the nanofibers unused.

To utilize the internal volume, a direct method of electrospinning an enzyme-containing polymer solution has been suggested, but prior work has been limited to the use of enzymes with water soluble polymers. The use of an aqueous solvent-based system leads to enzyme leaching into the aqueous solutions, which severely limits the use of these biocatalytic nanofibers as biosensors for clinical applications. Specifically, the enzyme loading is diminished significantly, rendering use as a biosensor very limited. Recently, Herricks et. al., J. Mater. Chem. 2005, 15, 3241, resolved this enzyme leaching by solubilizing the enzyme in an organic solvent by forming an ion pair complex. The work of Herricks et al. involved the covalent binding of the enzyme with the polymer, followed by electrospinning the mixture. The covalent bonds, however, reduce the enzyme loading capacity. In addition, the work of Herricks et al. is limited to biocatalytic applications, and has not been applied for use in the biosensor field, predominantly due to continued limitations with regard to loading capacity and retention.

Compared to surface attachment, physical entrapment achieves higher enzyme loadings. Materials with high enzyme loading and low mass transfer limitation are desirable for fast and sensitive biosensing applications. The term "mass transfer limitation" refers to the restriction of contact between the reaction media and the enzyme due to physical entrapment or other like conditions. While different kinds of materials have been used to achieve high enzyme loading by encapsulation, most possess mass transfer resistances, as most entrapped enzymes are not exposed to the reaction media in a manner that facilitates the reaction taking place. Previous trials have focused on developing single membrane biosensing material to reduce mass transfer limitations, however these materials could not achieve high enzyme loading. In these trials, the solubilized enzyme was covalently bound with water-insoluble polymer to form a homogenous mixture in an organic solvent. This homogenous mixture was then electrospun to form nanofibers. However, as with the work of Herricks et al., the covalent bonds interfered with enzyme loading, resulting in the highest enzyme loading thus far achieved by this method being 6.3%, w/w basis of the polymer.

In contrast, in one embodiment of the invention, enzyme-loaded nanofibers that contain an enzyme concentration in excess of 6.3%, and up to 30%, w/w basis of the polymer, have been fabricated by an electrospinning process wherein the electrospinning fluid is a non-aqueous polymer solution having an organic-soluble enzyme component, the solution capable of producing nanofibers with entrapped enzymes such that up to 30% enzyme loading, w/w basis of the polymer, is achieved. In order to achieve this high enzyme loading, and thus to overcome the foregoing drawbacks in this regard, in one embodiment of the present invention, entrapment of glucose oxidase (GOx) in polyurethane nanofibers is undertaken. Polyurethane (PU) represents a class of material that possesses a range of very desirable properties for use in biosensors. For example, PU is elastomeric, resistant to microorganisms and abrasion, and has excellent hydrolytic stability. Other materials equally well suited to use for the preparation of biosensors include, but are not limited to, cellulose acetate, polycarbonate, nafion, collagen, and synthetic materials such as polystyrene, poly(methyl methacrylate), and similar polymers, capable of being electrospun and functioning in a manner similar to the polyurethane exemplified herein.

In the exemplary embodiment presented, GOx is solubilized in the organic phase by forming an ion-pair complex with a surfactant. The solubilized GOx is then mixed with the polymer solution to form a homogenous solution, which can be directly electrospun. Because the system does not rely on the covalent bonding of the enzyme to the polymer, the concentration of entrapped enzyme, as compared to that in surface bound enzyme systems is greatly increased, at least from greater than 6.3% up to 30%. Further, because the enzyme loading has been so dramatically increased, the resulting high enzyme loaded biocatalytic nanofibers lend themselves readily to use as biosensors to detect very low concentrations of biological substances. The properties of this biosensor exhibit good stability and high sensitivity.

Solubilization and Stability of GOx in Organic Solvents

In another embodiment of the invention, enzymes were solubilized in organic solvents via either chemical modification with hydrophobic moieties or by physical complex formation with chemicals such as polymers, lipids, and ion-pairing with surfactants. Hydrophobic modification can lead to highly organic soluble enzymes (>44 mg-protein/ml) or to conjugation with polymers for interfacial assembly of enzymes. While each method has its own advantages, apart from ion-pairing, in most of the systems the enzyme is contained within either a micro aqueous environment and/or with a high concentration of modifiers. The presence of modifiers and/or water in oil-like conditions leads to problems downstream in the preparation of an homogenous electrospinning solution. In particular, it tends to generate an inhomogeneous electrospinning solution, which in turn leads to poor quality fibers that undermine the performance of the NEM as a sensitive biosensor. While these problems can be minimized by using low concentrations of surfactant and near anhydrous conditions achieved by ion pairing, an efficient ion pairing requires a stable electrostatic complex of surfactant. Unfortunately, the stability of the complex is influenced by several additional parameters, including pH, the type of solvent used, component concentrations, and phase ratio of aqueous to organic phase, among other parameters.

In one embodiment of the present invention, the effect of pH, solvent, GOx concentration in the aqueous phase, concentration of didodecyl diammoniumbromide (DDAB) in the organic phase and phase ratio are optimized to achieve maximum extraction of GOx into the organic phase. FIG. 1 summarizes the effect of different factors on GOx extraction into the organic phase. In this embodiment, acetate buffer at 20 mM concentration was utilized. The higher pH values outside the buffering range of this buffer were attained by preparing an acetate solution with acidic and basic components corresponding to pH.

The pH of the aqueous solution influences efficient ion pairing. GOx has a pH of 4.2, therefore at any pH below 4.2 the enzyme will be positively charged, resulting in very little or no ion pairing being possible with a cationic surfactant. This is evident from the low amount of enzyme extraction seen at pH below 4.2 (FIG. 1(a)). The little amount of enzyme that is extracted in the pH range below 4.2 is due to ion pairing with the small amount of negative charges on the enzyme surface.

Figure 2:
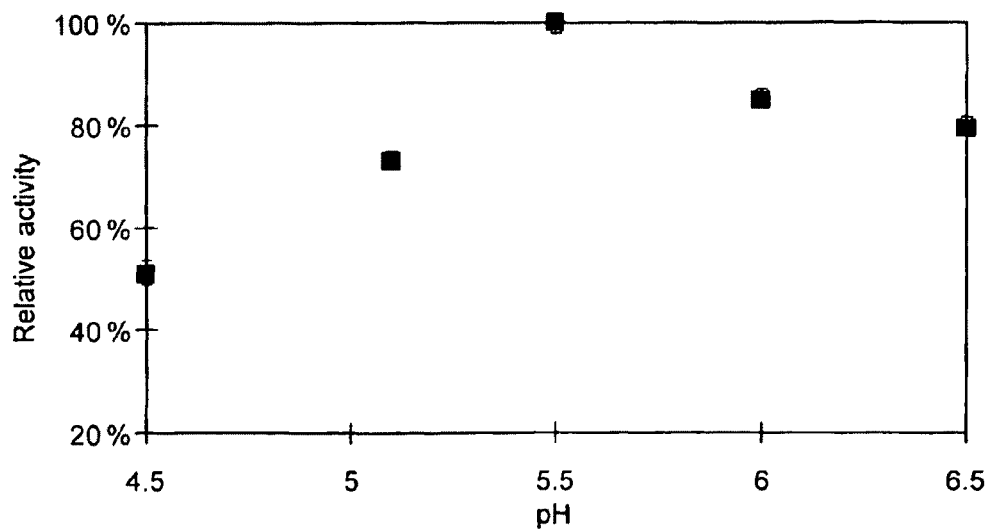
FIG. 2 is a graph of pH vs. relative enzyme activity and demonstrates the effect of pH on GOx activity.

As the pH of the aqueous solution is increased, the GOx becomes more negative, which facilitates better ion pairing with the cationic surfactant. However, as the pH is further increased, the increased attraction between the cationic surfactant and the negatively charged inner peptides of the GOx leads to changes in the folding structure of the enzyme. This, in turn, leads to denaturation and precipitation of GOx, thereby decreasing the amount of GOx extracted. This is seen in FIG. 1(a), where it is seen that at pH 5.5, the maximum amount of GOx is extracted. This corresponds to that point where the pH is high enough to have a negatively charged GOx and still low enough not to increase the attraction of surfactant and enzyme to a level that alters the three dimensional structure of the enzyme leading to reduced extraction. This is supported by the pH-dependent activity of native GOx as seen in FIG. 2.

In addition to pH, the nature of the solvent used is also important for the extraction of the enzyme. FIG. 1(b) indicates the effect of solvent on GOx extraction. The free energy change for the extraction process favors a solvent with the least polarity. The hydrophobicity of DDAB in the GOx-DDAB ion pair makes it easily extractable into a solvent that has weak interaction with water. Among solvents in which DDAB is soluble, for example, benzene, dichloromethane, chloroform and toluene, toluene has the lowest polarity index at 2.4. This makes toluene an effective solvent for extraction.

The concentration of DDAB in the organic solvent also has a significant effect on GOx extraction, data for which is set forth in FIG. 1(c). A lower concentration of DDAB is not sufficient to extract GOx from the aqueous phase. The critical micelle concentration (CMC) of DDAB in water is 15 mM. Therefore, the concentration of DDAB is maintained lower than the CMC value. Maximum extraction occurred at 2 mM DDAB. Above this concentration, due to the lack of a sufficient amount of GOx, the DDAB-GOx complex forms aggregates instead of solubilizing into the organic phase.

Similarly, the concentration of enzymes in the aqueous phase influences ion-pairing efficiency. Looking at FIG. 1(d), a high concentration of GOx in the aqueous phase leads to more enzyme-enzyme interactions, which hinders efficient ion pairing with DDAB. At lower enzyme concentrations, the absolute amount of enzyme extracted is low. A concentration of 0.7 mg/ml results in high extraction and a sufficient amount of enzyme in the organic phase.

FIG. 1(e) explores the effect of the phase ratio on the extraction of GOx into an organic solvent. Lower phase ratios of the organic phase contain lower amounts of DDAB available for extraction. This leads to lower extraction of GOx. At higher ratios of the organic phase, the concentration of DDAB in the organic phase is maintained at 2 mM, and the absolute amount of DDAB is increased with phase ratio. The higher amount of DDAB leads to aggregate formation of the DDAB-GOx complex as previously noted. This again, therefore, leads to lower extraction. In light of the foregoing, it is concluded that for this exemplary system, at a phase ratio of 1:1 with 2 mM DDAB in toluene organic solvent, and with 0.7 mg/ml of GOx in 5.5 pH acetate buffer, optimum extraction of GOx in the organic solvent is achieved. The foregoing principles are equally applicable to other systems based on the characteristics and interaction of bio agent, solvent, concentration, pH, and any other affecting parameters.

In other embodiments, other surfactants such docusate sodium salt (AOT), cetyltrimethylammonium bromide (CTAB) and sucrose monododecanoate were investigated. AOT, being an anionic surfactant, did not extract GOx above pH 4.2. Below a pH of 4.2 the conditions were too acidic for the enzyme. CTAB, though cationic, did not have enough hydrophobicity to extract the enzyme into the organic phase. Sucrose monododecanoate, being non-ionic and soluble in the aqueous phase, did not result in extraction of GOx in the organic phase.

Once extracted, the enzyme was dried and re-dissolved in an electrospinning solution in accord with the invention. The nature of the electrospinning solution had a significant impact on the extracted enzyme's activity. An important consideration in fabrication of NEMs is the ability of the material to maintain the activity of the extracted enzyme. Therefore, determination of an optimum solution involves careful choice of solvent(s) for preparing the polymer-enzyme electrospinning solution. With regard to the GOx example being used herein, choice of solvent was made after a study of the stability of the extracted enzyme in different solvents was conducted.

Figure 3:
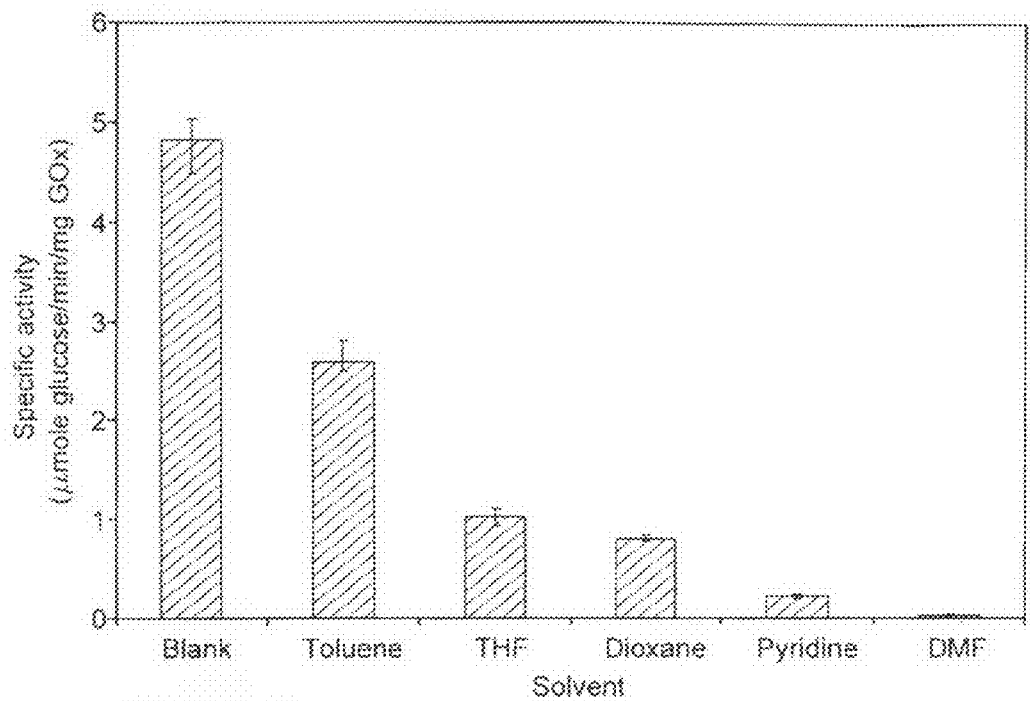
FIG. 3 is a graph of various solvents vs. specific activity and demonstrates the effect of each solvent on organic-soluble GOx stability.

FIG. 3 summarizes the effect of potential solvents on solubilized GOx activity. The solubilized enzyme was incubated with a solvent for 24 hours at room temperature. The activity of the solubilized enzyme was found to decrease as the solvent polarity increased. This is likely due to the fact that the solvents with higher polarity compete for the intrinsic water of hydration of the enzyme, thereby, denaturing the enzyme. Toluene, which exhibits a relatively low polarity index comparatively, resulted in activity closer to that of an enzyme not incubated with any solvent. Therefore, in this embodiment, preparation of electrospinning solution was conducted using only toluene and THF, though one skilled in the art may for various reasons choose to employ other solvents meeting the necessary criteria with regard to retention of enzyme activity. Such solvents might include pyridine, benzene, and DMF, among others.

Fabrication of NEMs by Electrospinning

High enzyme loading and homogenous material distribution in the NEMs are important criteria in the development of sensitive biosensors. The fabrication process used herein for the NEMs was chosen to achieve these desired biosensor material properties. Electrospinning fabrication techniques were proven most effective in achieving the desired design, though other suitable methods, such as preparing the nanofibers by the gas jet (NGJ) process described in U.S. Pat. No. 6,382,526, U.S. Pat. No. 6,520,425, and U.S. Pat. No. 6,695,992 might also be used.

Figure 4:
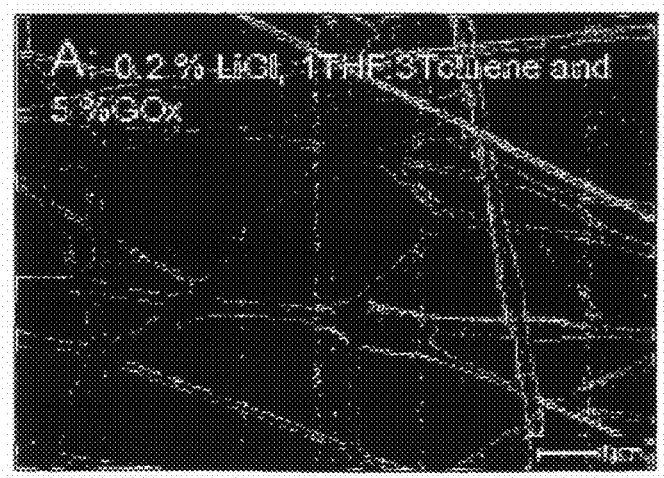
FIG. 4a is a micrograph of the effect of 0.2% Salt, 1THF: 3Toluene and 5% GOx on fiber quality.
FIG. 4b is a micrograph of the effect of 0.2% Salt, 3THF: 1Toluene and 5% GOx on fiber quality.
FIG. 4c is a micrograph of the effect of 0% Salt, 3THF: 1Toluene and 5% GOx on fiber quality.
FIG. 4d is a micrograph of the effect of 0% Salt, 1THF: 3Toluene and 5% GOx on fiber quality.
Figure 4:
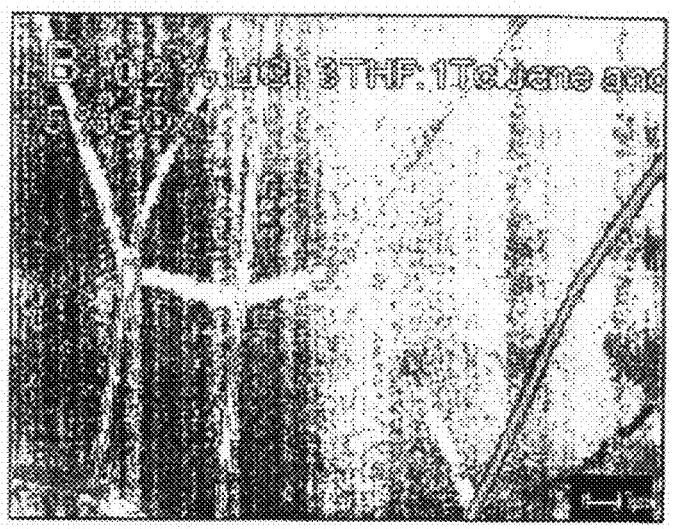
Figure 4:
Figure 4:
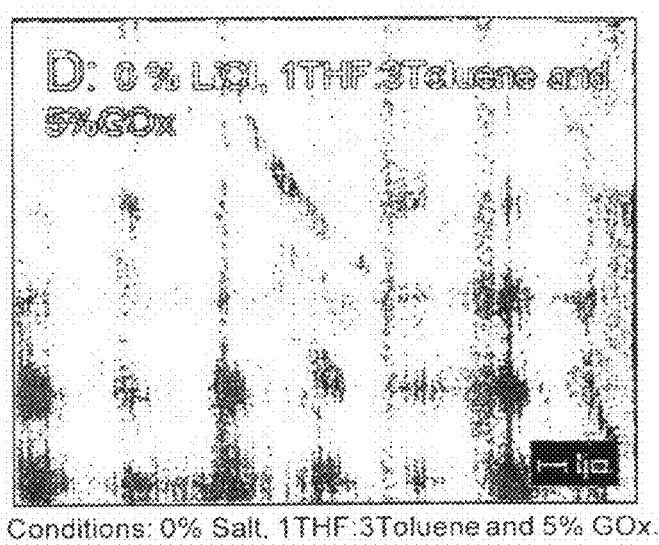

As expected, the process of electrospinning a mixture of polymer-enzyme solution is influenced by various factors. For example, the presence of compounds with a high degree of difference in physical and electrochemical properties in the polymer-enzyme solution requires a careful selection of electrospinning conditions that satisfy the primary criteria of achieving high loading of the enzyme on nanofibers without compromising the integrity of the spun nanofiber. FIG. 4 details the effect of various factors on the quality of the resulting NEMs. The low activity of GOx with solvents like tetrahydrofuran (THF) that dissolve polyurethane resulted in the use of toluene as a co-solvent during electrospinning for this system. Electrospinning a polymer-enzyme solution having more than 5% (w/w of polymer) enzyme content resulted in particle formation in the electrospun NEMs. The particle formation during electrospinning lead to non-homogenous distribution of GOx in the nanofibers. However, given that the stationary polymer-enzyme solution is homogenous, it was determined that the particle formation during electrospinning was due to the difference in the flow properties of substances in the polymer-enzyme solution.

To overcome this, the polymer-enzyme solution was made using a single solvent, for example, THF or pyridine. However, it was found that particles would still form in the nanofiber. This is due to the denaturation of GOx by the solvent that leads to separation of the enzyme from the polymer in the electrospinning solution. This also resulted in particle formation. While the addition of salt (LiCl) helped to eliminate the problem by increasing the charge in the solution and making it more homogenous, a higher concentration of LiCl (2 wt %) resulted in very thick fibers. To address these potential drawbacks, the polymer-enzyme solution was prepared to include a combination of THF and toluene to increase the activity of GOx, and salt was added in low concentration, on the order of about 0.2 wt %, to reduce the precipitation of enzyme during electrospinning.

In addition to the foregoing, physical conditions, such as speed of electrospinning, humidity, and electrical conditions such as field strength, further influence the quality of the electrospun fiber. The speed of electrospinning has an effect on fiber formation as higher speeds lead to more bead formation. At higher speeds, the polymer does not have enough time to be stretched into a fiber, and as a result more beads are formed. At lower speeds, the process is very slow and quicker evaporation of solvent leads to choking of the jet, thereby affecting the integrity of the fiber. The humidity of the spinning environment alters the rate of solvent evaporation during electrospinning. For example, low humidity leads to quicker evaporation of solvent leading to constant choking of the nozzle of the jet. This effect can be compensated for by increasing the speed of electrospinning. An electrospinning speed of 2 μl/min was found to produce good fibers with minimal choking of the jet.

The electric field strength must also be optimized. Higher field strengths lead to the formation of thicker fibers and lower field strengths lead to the formation of more beads. An electric field strength of about 1 KV/cm resulted in the formation of quality fibers, depending on the remaining parameters being optimized.

Based on the foregoing, in one embodiment, a NEM was fabricated having enzyme loadings as high as 30% GOx in the nanofiber. In previous work, a theoretical loading maximum of only 11% monolayer coverage was predicted, with actual chemical attachment of the enzyme to the polymer fiber surface reported at a maximum of 6.3% w/w of the polymer. The higher enzyme loading of the current invention is achieved by utilizing the inner volume of the nanofiber mat through encapsulation of enzymes in the nanofibers and electrostatic interaction between the charged enzyme and polymer fiber at the molecular level. The ability to generate such a product is a characteristic unique to the direct electrospinning of the polymer-enzyme solution, which in this embodiment was a PU/GOx system.

The effective encapsulation of enzymes inside NEMs was assessed by incubating the NEM in a buffer at room temperature under stirring. At regular intervals, a sample from the incubation mixture was centrifuged and the supernatant was analyzed for GOx. The supernatant did not exhibit any GOx activity, indicating efficient entrapment of GOx by the nanofibers.

Apart from the high enzyme loading and the homogenous material distribution in the NEM with effective encapsulation, the activity of enzymes in the NEM is critical to sensitive biosensor development. The specific activity of the NEM was monitored with respect to enzyme loading and weight of the nanofiber sheet. The weight was increased by increasing the collection time of the nanofibers, which in turn increased the thickness of the collected nanofiber sheet. As the NEM became thicker, increased mass transfer limitations for reactants and products were generated.

The activity assays of the NEM provide data relative to the effect of extreme electrospinning conditions on the specific activity of GOx. The perspective of mass transfer limitations on catalytic efficiency of the NEM provides an insight into corresponding biosensor performance. In one embodiment, the highest observed, activity of the NEM was 0.15 U/mg, as seen in Table 1. The weight of the NEM had an influence on the initial activity of nanofibrous enzyme. From Table 1, the reduction in activity for 5% and 20% enzyme loadings are similar based on the weight of the collected nanofibers. This indicates that the activity reduction is due to the mass transfer limitation increase with more fibers.

Figure 5:
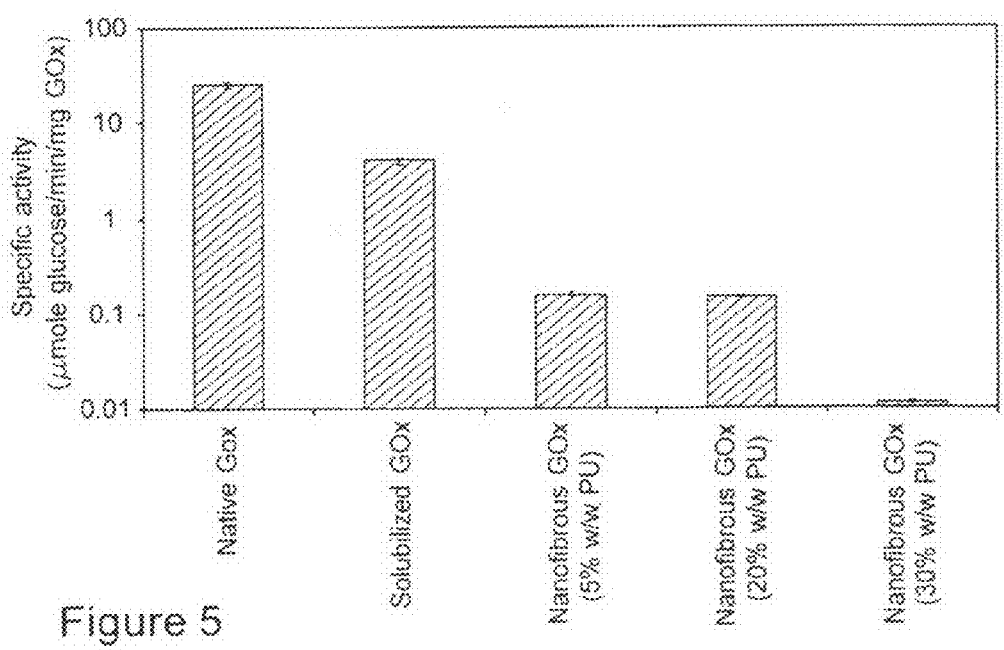
FIG. 5 is a graph illustrating the specific activity of different forms of GOx.

As is shown in FIG. 5, the specific activity did not change appreciably with increased enzyme loading from 5% to 20%, suggesting that filling the inner volume of the nanofibers with GOx does not affect the intrinsic activity of nanofibrous enzymes. However, as the enzyme loading increased to 30%, the activity dropped sharply. The nanofiber with 30% enzyme contained more non-active enzymes, due to the fact that at such a high enzyme concentration in the electrospinning solution, the GOx was more easily denatured by the THF. The denatured enzyme in turn accelerated the denaturation of other active enzymes by forming aggregates, and ultimately causing precipitation of the enzyme in the polymer-enzyme solution during electrospinning. The maximum amount of enzyme loading achievable was determined by the phase behavior of the polymer-enzyme solution.

TABLE 1

Effect of Enzyme Loading and Spinning Time on Nanofibrous Enzyme Activity

| Enzyme loading (wt % of PU) | Weight of NEM (mg) | Activity of GOx in NEM based on amount of enzyme ($\mu$mole glucose min$^{-1}$ mg GOx$^{-1}$) | Activity of GOx in NEM based on weight of nanofibers ($\mu$mole glucose min$^{-1}$ mg NEM$^{-1}$) |
|---|---|---|---|
| 5 | 0.12 | 0.154 | 0.008 |
| 5 | 0.3 | 0.097 | 0.005 |
| 5 | 0.54 | 0.052 | 0.003 |
| 20 | 0.12 | 0.146 | 0.029 |
| 20 | 0.3 | 0.08 | 0.016 |
| 20 | 0.54 | 0.01 | 0.002 |
| 30 | 0.12 | 0.011 | 0.003 |
| 30 | 0.3 | 0.006 | 0.002 |
| 30 | 0.54 | 0.002 | 0.001 |

NEM as a Biosensor

Figure 6:
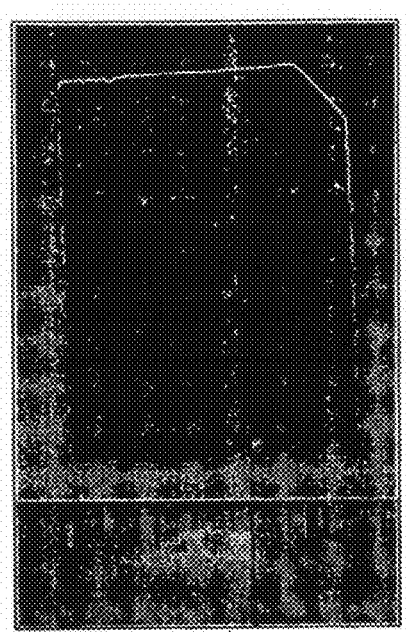
FIG. 6 is a photograph of a nanofiber spun over carbon paper.

Traditional biosensors relative to GOx involve the immobilization of GOx over metallic or carbon transducers to monitor the current associated with the release of $H_2O_2$. In one embodiment of the present invention, the nanofibers were spun onto carbon electrodes (FIG. 6) used to evaluate the electrochemical properties of the NEM. The surfactant-stabilized enzyme was water insoluble to eliminate the problem of enzyme leaching during the biosensor application in aqueous environments. The combined effects of high enzyme loading and single membrane biosensors allow development of very sensitive biosensors. In addition to the enzyme activity and loading, the electrochemical properties of the NEM influenced its application as a biosensor. The electrochemical signal transduction ability of the NEM was monitored by employing cyclic voltammetry and sensitivity was evaluated amperometrically at a potential of 0.69V.

Figure 7:
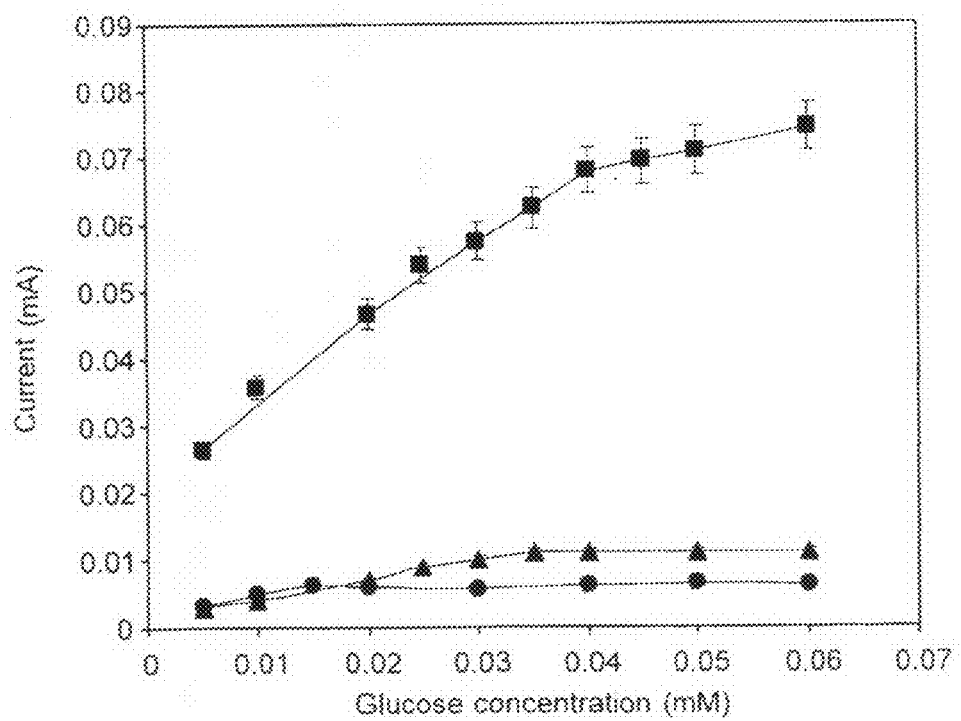
FIG. 7 is a graph of glucose concentration vs. current measured at 0.69V at varied enzyme loading levels.

FIG. 7 shows the current response of the NEM electrode. The current was measured at 0.69V with respect to the reference electrode. At 0.69V, the hydrogen peroxide produced by enzymatic oxidation of glucose was oxidized at the NEM electrode. The electron released from this reaction was detected amperometrically. As expected, the current increased with an increase in enzyme loading up to a concentration of 20%. At 30% enzyme loading, however, a decrease in current is observed due to the bulk of the denatured enzyme present in the NEM. This result is analogous to the activity assay of NEM, i.e., at a very high enzyme loading, precipitation of the enzyme occurs in the electrospinning solution, which causes inactive enzymes in NEM.

The NEM has a very high sensitivity as compared to previously reported results, as sown in Table 2. The NEM according to the invention demonstrated sensitivity almost 100 times greater based on enzyme weight, and almost 10 times higher based on the surface area of the biosensor. A sensitivity of 0.39 AM$^{-1}$ cm$^{-2}$ and 66.6 AM$^{-1}$ mg GOx$^{-1}$ is shown in the linear range of operation. In general, the sensitivity for biosensors employing either nanostructured materials or membranes is reported only to be in the range of $10^{-5}$ to $10^{-2}$ AM$^{-1}$ cm$^{-2}$ based on biosensor weight and from 0.03 to 0.5 AM$^{-1}$ mg GOx$^{-1}$ based on amount of enzyme. This high sensitivity was observed in the linear range up to 40 $\mu$M glucose with the lower detection limit of 5 $\mu$M. These values are comparable to glucose levels available for non-invasive transdermal blood glucose level measurements. It was also seen that with increases in weight, the dynamic range of the biosensor was increased. The higher diffusion limitation with thicker fibers makes the reaction between the enzyme and the glucose mass transfer controlled, increasing the dynamic range of the analysis.

TABLE 2

Performance of Nanofibers as Glucose Biosensor.

| Enzyme loading (wt % of PU) | Weight of NEM (mg) | Detection limit (mM) | Dynamic range (mM) | Biosensor sensitivity (AM$^{-1}$ cm$^{-2}$) | Biosensor sensitivity (AM$^{-1}$ mg GOx$^{-1}$) |
|---|---|---|---|---|---|
| 5 | 0.12 | 0.005 | 0.02 | 0.11 | 39.2 |
| 5 | 0.3 | 0.005 | 0.04 | 0.06 | 18.5 |
| 5 | 0.54 | 0.005 | 0.04 | 0.06 | 12.4 |
| 20 | 0.12 | 0.005 | 0.04 | 0.39 | 66.6 |
| 20 | 0.3 | 0.005 | 0.06 | 0.26 | 14.3 |
| 20 | 0.54 | 0.005 | 0.1 | 0.04 | 2.3 |
| 30 | 0.12 | 0.005 | 0.03 | 0.09 | 13.3 |
| 30 | 0.3 | 0.005 | 0.04 | 0.07 | 3.3 |
| 30 | 0.54 | 0.005 | 0.1 | 0.07 | 1.1 |

The sensitivity of the biosensor according to this invention is increased as compared to that reported in the literature for glucose biosensors employing different nanostructured materials. The sensitivity was not appreciable at lower enzyme loading, where the electron transfer from the enzyme to the electrode was reduced by the polyurethane fiber. However, at higher enzyme loading the enzyme was more uniformly distributed over and throughout the fiber, thereby reducing the problems associated with electron transfer.

Figure 8:
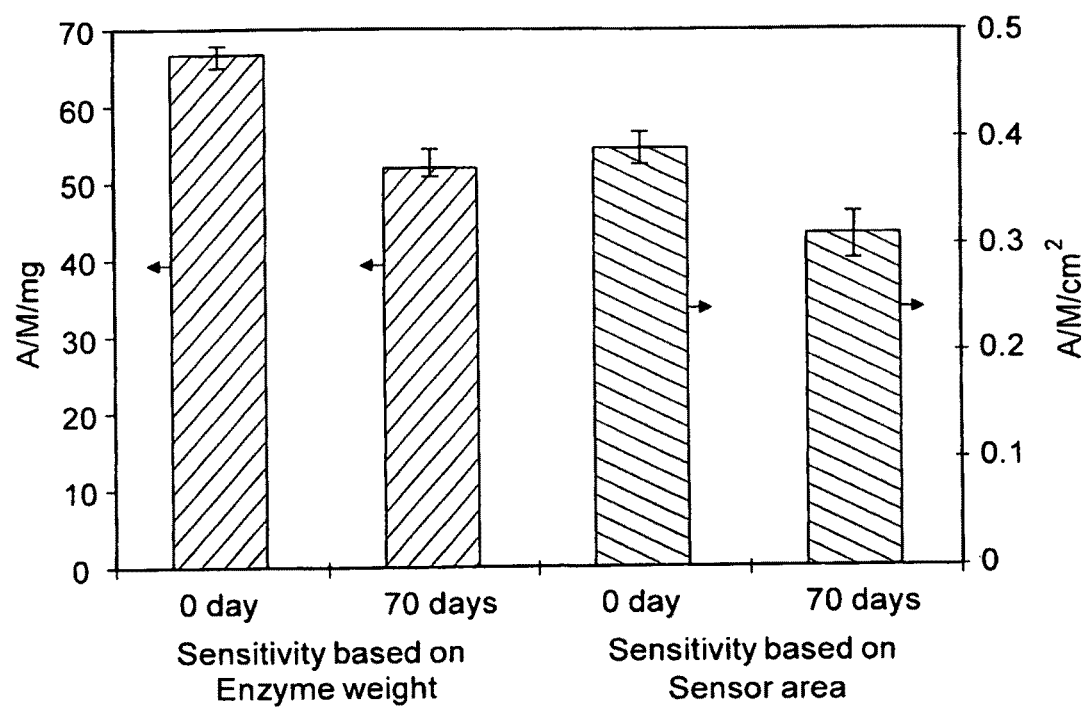
FIG. 8 is a graph of illustrating the effect of storage at 4° C. on NEM sensitivity based on enzyme weight and sensor area.

Additionally, the NEM demonstrates reusability, which is very advantageous. In this regard, the sensitivity was retained even after six continuous cycles. The storage stability of the biosensor was assayed by storing the biosensor at 4° C. (FIG. 8). Under these conditions, even after 70 days, the biosensor had retained 80% of its sensitivity.

As has been demonstrated, the direct electrospinning method for the fabrication of enzyme-carrying nanofibers can be applied for the development of biosensors. A comprehensive optimized procedure for the maximum solubilization of GOx in an organic solvent, coupled with direct electrospinning, resulted in a very high loading of GOx in the NEM. The aqueous-insoluble nature of the enzyme prevents it from leaching into aqueous solution during catalytic applications. The high enzyme loading and low mass transfer limitations of the NEM, with effective entrapment of GOx, results in high biocatalytic efficiency. The versatility of this technique provides for the development of highly sensitive, stable and reproducible biosensors. Another embodiment outside the biosensor realm involves NEMs being effectively used in different catalytic and electrochemical applications, for example in biofuel cells.

The following experimental methods were used in generating the foregoing data. They are provided here for the convenience of the skilled technician with regard to generating materials in accord with the invention claimed.

Experimental Method of Determining Solubilization of Glucose Oxidase in Organic Solvent Unless otherwise specified, the extraction of GOx is performed with the following typical procedure. An aqueous phase consisting of 10 ml of 0.7 mg/mL glucose oxidase and 20 mM acetate buffer of pH 5.5 was prepared. The solution was then contacted under stirring at 300 rpm and 25° C. for 2 minutes with 10 ml of toluene that contained 2 mM DDAB. Phase separation was achieved by centrifugation. The organic soluble enzyme was then dried by bubbling $N_2$ through the solution to give an enzyme-surfactant ion-paired complex that was dissolved in different organic solvents. The concentration of GOx in the organic phase was determined spectrophotometrically at 450 nm by monitoring the yellow color of FAD attached to the enzyme.

Experimental Method of Electrospinning

A polymer-enzyme solution was prepared at room temperature by dissolving polyurethane (PU) in a mixture of tetrahydrofuran (THF) containing 0.2 wt % LiCl and toluene (3:1 v/v), containing ion-paired DDAB-GOx complex. The polymer-enzyme solution was electrospun with electric field strength of 1 kV/cm. A teflon capillary tube with an orifice diameter of 0.5 mm was used as the jet. Fibers were collected on carbon paper used as an electrode in a biofuel cell. The weight of the carbon paper was measured before and after the collection of electrospun fibers to monitor the net weight of accumulated fibers with enzymes. The amount of GOx in the fiber corresponded to the ratio of polymer-to-enzyme in the solution.

Experimental Method of Measuring Enzyme Activity

The activity of GOx in nanofibers was measured using glucose as the substrate in pH 5.1, 100 mM acetate buffer. The reaction with nanofibrous GOx was conducted in 50-mL vials. Nanofibers with known weight were added to 30 mL of 1M glucose solution containing 0.2 mg horseradish peroxidase and 2 mg O-dianisidine. The time course of the reaction catalyzed by the nanofibrous GOx was obtained spectrophotometrically by measuring the absorbance of 1 ml aliquots taken from the reaction mixture at constant time intervals.

Experimental Method of Determining Enzyme Stability in Organic Solvent

GOx solubilized in toluene was dried by passing $N_2$ to remove toluene and re-dissolved into different solvents, including THF, pyridine, DMF and dioxane. The solvents were chosen such that both PU and DDAB were soluble therein. The re-dissolved GOx in the various solvents was incubated at room temperature (22° C.) for 24 hours. The incubation was stopped by purging $N_2$ to remove the solvent. The activity was then measured using glucose as a substrate in an aqueous buffer, in keeping with the procedure set forth above.

Experimental Methods of Electrochemical Experiments

A three-electrode electrochemical cell was used to evaluate the potential use of enzyme-loaded nanofibers as biosensors. The cell consisted of a Model CH111, available from CH Instruments, Austin, Tex., a platinum-wire counter electrode, and a modified working electrode made with fiber-coated over a carbon paper. The cyclic voltammograms of the sensor were obtained in a phosphate buffer solution (pH 7.0, 0.5M). The sensitivity of the biosensor was monitored amperometrically at the potential of +0.69 V versus a Ag/AgCl reference electrode. The cell was operated at room temperature, in an $O_2$ purged unstirred solution and calibrated with different concentrations of glucose. The glucose solution of unknown concentration was then analyzed at this voltage. After applying the desired working potential, enough time was allowed for the cell to react with the oxygen.

The foregoing experimental parameters and set-ups were used to generate the data and information provided herein in support of the claimed invention. Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A method for producing a biosensor comprising solubilizing one or more enzymes in an organic solvent by modification of the one or more enzymes with a hydrophobic moiety or by formation of a physical complex with a hydrophobic moiety or a surfactant; dissolving said one or more organic solubilized enzymes in a non-aqueous polymer solution, wherein said one or more organic solubilized enzymes comprise more than 6.3% and up to 30% by weight of said non-aqueous polymer solution, wherein said solubilized enzymes are not covalently bonded to a polymer in said non-aqueous polymer solution; and encapsulating said one or more solubilized enzymes in said polymer by electrospinning the polymer solution including the one or more organic solubilized enzymes to form at least one electrospun fiber having said one or more enzymes entrapped within and homogeneously distributed throughout the fiber composition.

2. The method of claim 1 wherein the organic solubilized enzymes comprise an enzyme capable of catalyzing a reaction with at least one target chemical reactant selected from the group consisting of sugars, organic acids, and urea.

3. The method of claim 1 wherein the non-aqueous polymer solution includes at least one solvent selected from the group consisting of tetrahydrofuran (THF), pyridine, benzene, dimethylformamide (DMF), and toluene, and combinations thereof.

4. The method of claim 1 wherein the biosensor is in the form of a membrane, a rod, a wire, a mat, a hierarchical structure, a sleeve, a stent, or a particle.

5. The method of claim 1 wherein said one or more organic solubilized enzymes comprise no more than 25% w/w of the polymer solution.

6. The method of claim 1 wherein said one or more organic solubilized enzymes comprise from about 20% to 30% w/w of the polymer solution.

7. A method for producing electrospun fibers having entrapped enzymes homogeneously distributed throughout their composition comprising:

(a) preparing a non-aqueous polymer solution;
(b) solubilizing one or more enzymes in an organic solvent by modification of the one or more enzymes with a hydrophobic moiety or by formation of a physical complex with a hydrophobic moiety or a surfactant;
(c) adding the one or more solubilized enzymes to the non-aqueous polymer solution, wherein said one or more solubilized enzymes comprise more than 6.3% and up to 30% by weight of said non-aqueous polymer solution, wherein none of said solubilized enzymes are covalently bonded to a polymer in said non-aqueous polymer solution;
(d) charging the solution from step (c) to a reservoir in fluid communication with an electrospinning device;
(e) releasing the solution from the reservoir to the electrospinning device;
(f)—operating the electrospinning device, under the influence of an electric field, to produce a jet of fluid comprising the non-aqueous polymer solution of step (d), said jet of fluid forming polymer fibers having entrapped enzymes homogeneously distributed throughout their composition; and
(g)—collecting the polymer fibers having entrapped enzymes homogeneously distributed throughout their composition.

8. The method of claim 7 further including the step of using the fiber as a biosensor.

9. The method of claim 7 wherein said non-aqueous polymer solution contains polyurethane.

10. The method of claim 7 wherein said one or more solubilized enzymes comprises glucose oxidase.

11. The method of claim 7 wherein said one or more solubilized enzymes comprise no more than about 25% w/w of the solution of step (c).

12. The method of claim 7 wherein said one or more solubilized enzymes comprise more than 6.3% and up to 30% w/w of the solution of step (c).

13. The method of claim 1 wherein said one or more organic solubilized enzymes has been solubilized by chemical modification with one or more hydrophobic moieties.

14. The method of claim 1 wherein said one or more organic solubilized enzymes has been solubilized by forming a physical complex with one or more polymers or lipids or by ion pairing with one or more surfactants.

15. The method of claim 7 wherein said one or more solubilized enzymes of step (b) are solubilized by chemical modification with one or more hydrophobic moieties.

16. The method of claim 7 wherein said one or more solubilized enzymes of step (b) are solubilized by forming a physical complex with one or more polymers or lipids or by ion pairing with one or more surfactants.

17. The method of claim 1 further comprising contacting said at least one fiber with a metal or carbon transducer.

18. The method of claim 7 further comprising contacting said polymer fibers containing the one or more enzymes with a metal or carbon transducer.

19. The method of claim 7 further comprising adding a salt to the solution of step (c).

\* \* \* \* \*